United States Patent [19]

Fürst et al.

[11] 4,285,880
[45] Aug. 25, 1981

[54] D-HOMOPREGNANES

[75] Inventors: Andor Fürst, Basel; Peter Keller, Reinach; Marcel Müller, Frenkendorf, all of Switzerland

[73] Assignee: Hoffmann-La Roche Inc., Nutley, N.J.

[21] Appl. No.: 82,269

[22] Filed: Oct. 5, 1979

Related U.S. Application Data

[62] Division of Ser. No. 921,036, Jun. 30, 1978, Pat. No. 4,202,823.

[30] Foreign Application Priority Data

Jul. 6, 1977 [LU] Luxembourg .............. 77699

[51] Int. Cl.³ ............................................. C07J 63/00
[52] U.S. Cl. .............................................. 260/455 R
[58] Field of Search ...................... 260/455 R; 562/498

[56] References Cited

U.S. PATENT DOCUMENTS

| | | | |
|---|---|---|---|
| 3,766,213 | 10/1973 | Furst et al. | 260/343.6 |
| 3,920,703 | 11/1975 | Alig et al. | 260/343.6 |
| 4,140,700 | 2/1979 | Furst et al. | 260/343.6 |

FOREIGN PATENT DOCUMENTS

| | | |
|---|---|---|
| 2424752 | 12/1975 | Fed. Rep. of Germany . |
| 2756654 | 6/1978 | Fed. Rep. of Germany . |

*Primary Examiner*—Henry R. Jiles
*Assistant Examiner*—Natalia Harkaway
*Attorney, Agent, or Firm*—Jon S. Saxe; Bernard S. Leon; James H. Callwood

[57] ABSTRACT

D-Homopregnanes of the formula

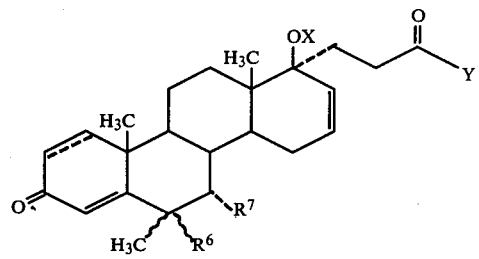

wherein X is hydrogen, Y is hydroxy or X and Y taken together denote an oxygen to carbon bond; $R^6$ is hydrogen, $R^7$ is hydrogen, lower alkanoylthio or aroylthio, or $R^6$ and $R^7$ taken together denote a carbon to carbon bond and the dotted line in the 1,2-position of the A-ring together with the corresponding solid line denotes a single or double carbon to carbon bond or a pharmaceutically acceptable basic addition salt thereof when Y is hydroxy having diuretic activity are disclosed.

1 Claim, No Drawings

D-HOMOPREGNANES

This is a division, of application Ser. No. 921,036 filed June 30, 1978, now U.S. Pat. No. 4,202,823.

DESCRIPTION OF THE INVENTION

The present invention relates to D-homosteroids. More particularly, the invention is concerned with D-homopregnanes, a process for the preparation thereof and pharmaceutical compositions containing same.

The D-homosteroids provided by the present invention are compounds of the general formula

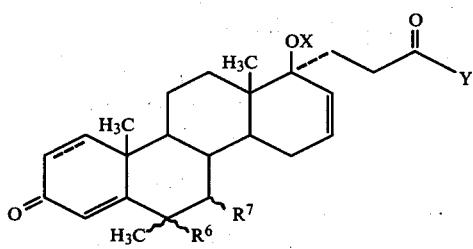

(I)

wherein X is hydrogen, Y is hydroxy or X and Y taken together denote an oxygen to carbon bond; $R^6$ is hydrogen, $R^7$ is hydrogen, lower alkanoylthio or aroylthio, or $R^6$ and $R^7$ taken together denote a carbon to carbon bond and the dotted line in the 1,2-position of the A-ring together with the corresponding solid line denotes a single or double carbon to carbon bond or a pharmaceutically acceptable basic addition salt thereof when Y is hydroxy.

As used throughout the specification and appended claims, the term "alkanoylthio" denotes the residue obtained by removal of the thiol proton of the thiolcarboxylic acid group (COSH) of straight- or branched-chain, saturated or unsaturated aliphatic thiolcarboxylic acids. Examples of the aforementioned alkanoylthio groups which contain preferably from 1 to 15 carbon atoms are formylthio, acetylthio, propionylthio, butyrylthio, pentanoylthio, hexanoylthio, undecylenoylthio, oleoylthio, cyclohexylpropionylthio, cyclopentylpropionylthio and phenacetylthio. The term "aroylthio" denotes the residue obtained by removal of the thiol proton of the thiolcarboxylic acid group (COSH) of aromatic thiolcarboxylic acids. An example of the aforementioned aroylthio group is benzoylthio. The term "lower" denotes a group having a carbon skeleton containing 1 to 7 carbon atoms.

In the formulas presented herein, the various substituents are joined to the cyclic nucleus by one of three notations: a solid line (—), indicating a substituent which is in the β-orientation (above the plane of the paper), a dotted line (---), indicating a substituent which is in the α-orientation (below the plane of the paper), or a wavy line (⁓), indicating a substituent which may either be in the α- or β-orientation. The position of the methyl groups in the 10- and 13-positions have been arbitrarily indicated as the δ-orientation which is consistent with the absolute stereochemistry of the products described in the examples. It is to be understood, however, that in the formulas presented both in the specification and in the appended claims, there is intended to be represented both of the enantiomeric series, as well as mixtures thereof, such as racemic mixtures.

As pharmaceutically acceptable basic addition salts of the acids of formula I, i.e., the homopregnanes of formula I wherein Y is hydrogen, there may be mentioned, in particular, alkali metal salts, e.g., sodium and potassium salts, ammonium salts and alkaline earth metal salts, e.g., calcium salts. The potassium salts are preferred.

The methyl group in the 6-position of the steroid nucleus may occupy the α- or β-configuration, the 6α-methyl configuration being preferred.

Preferred D-homopregnanes of formula I are those in which $R^7$ is lower alkanoylthio or aroylthio. Particularly preferred are those in which $R^7$ is lower alkanoylthio. Furthermore, the lactones of formula I, i.e., the compounds of formula I wherein X and Y taken together denote an oxygen to carbon bond, are preferred.

According to the process provided by the present invention, the D-homopregnanes, i.e., the compounds of formula I and their pharmaceutically acceptable basic addition salts are prepared by (a) hydrogenating or isomerizing a D-homopregnane of the formula

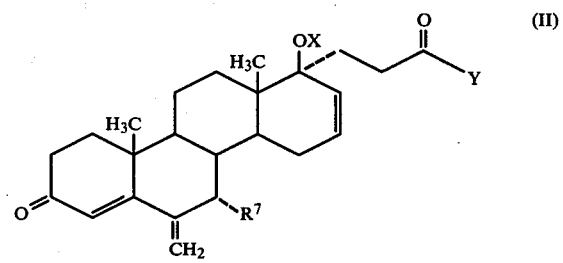

(II)

wherein X, Y and $R^7$ are as above, or a salt thereof, or (b) reacting a D-homopregnane of the formula

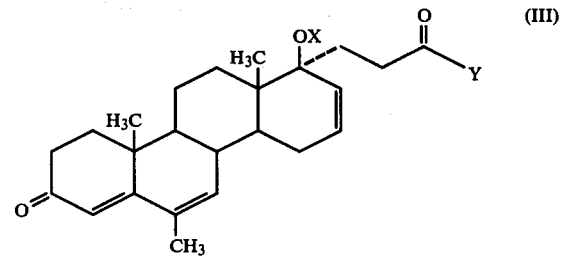

(III)

wherein X and Y are as above, or a salt thereof with a compound of the formula $R^7H$ wherein $R^7$ is as above, or (c) dehydrogenating a D-homopregnane of the formula

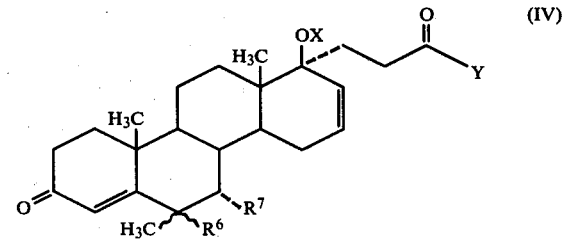

(IV)

wherein X, Y, $R^6$ and $R^7$ are as above, or a salt thereof in the 1,2-position and/or in the 6,7-position when $R^6$ and $R^7$ are each hydrogen, or (d) cleaving the lactone ring of a D-homopregnane of the formula

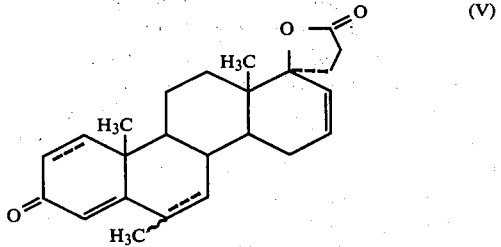

wherein the dotted lines in the 1,2-position of the A-ring and the 6,7-position of the B-ring each taken together with the corresponding solid lines denote a single or double carbon to carbon bond, or (e) lactonizing a D-homopregnane of the formula

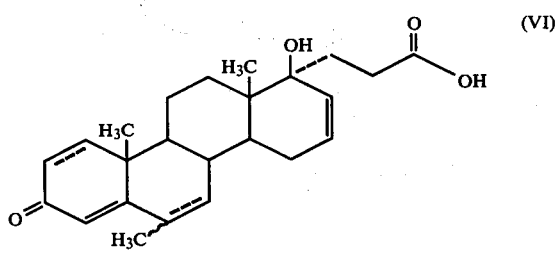

wherein the dotted lines in the 1,2-position of the A-ring and the 6,7-position of the B-ring each taken together with the corresponding solid lines denote a single or double carbon to carbon bond, or a salt thereof, or (f) oxidizing a D-homopregnane of the formula

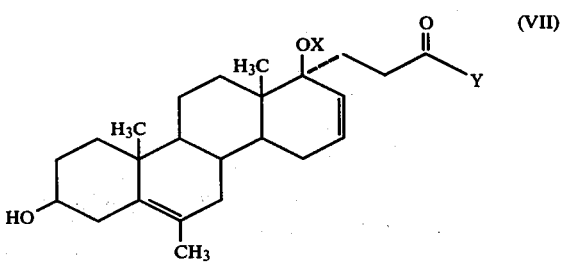

wherein X and Y are as above, or a salt thereof to give corresponding $\Delta^4$-, $\Delta^{4,6}$- or $\Delta^{1,4,6}$-3-ketones.

The hydrogenation of the 6-methylene group of the D-homopregnane of formula II according to embodiment (a) of the present process can be carried out by known methods using hydrogenation catalysts, e.g., noble metal catalysts, such as palladium.

The isomerization of the 6-methylene group of the D-homopregnane of formula II to a 6-methyl-$\Delta^6$-function can also be carried out by known methods, e.g., catalytically. Suitable isomerization catalysts are, e.g., metal hydrogenation catalysts, preferably palladium in ethanol. Expeditiously, a hydrogen donor, such as cyclohexane, is added to activate the catalyst. Undesired side-reactions, such as hydrogenations by means of the hydrogen donor can be avoided by buffering the mixture.

According to embodiment (a) of the present process, there are obtained D-homopregnanes of formula I in which $R^6$ and $R^7$ are each hydrogen or $R^6$ and $R^7$ taken together denote a carbon to carbon bond and the dotted line in the 1,2-position of the A-ring taken together with the corresponding solid line denotes a single carbon to carbon bond.

The introduction of the lower alkanoylthio or aroylthio group $R^7$ into the D-homopregnanes of formula III according to embodiment (b) of the present process can be carried out by known methods by reacting a D-homopregnane of formula III with a suitable thiocarboxylic acid. The reaction can be carried out in an inert solvent, such as an ether, e.g., dioxan or tetrahydrofuran, an alcohol, e.g., methanol or ethanol or a chlorinated hydrocarbon, e.g., chloroform. Alternatively, the thiocarboxylic acid may be used in excess to serve also as the solvent.

According to embodiment (b) of the present process there are obtained D-homopregnanes of formula I in which $R^6$ is hydrogen, $R^7$ is alkanoylthio or aroylthio and the dotted line in the 1,2-position of the A-ring taken together with the corresponding solid line denotes a single carbon to carbon bond.

The 1,2-dehydrogenation of the D-homopregnanes of formula IV according to embodiment (c) of the present process can be carried out by known methods. For example, microbiologically or by means of dehydrogenation agents, such as selenium dioxide, 2,3-dichloro-5,6-dicyanobenzoquinone, chloranil, thallium triacetate or lead tetraacetate. Suitable microorganisms for the 1,2-dihydrogenation are, e.g., Schizomycetes, particularly those of the genera Arthrobacter, e.g., A. simplex ATCC 6946, Bacillus, e.g., B. lentus ATCC 13805 and B. sphaericus ATCC 7055, Pseudomonas, e.g., P. aeruginosa IFO 3505, Flavobacterium, e.g., F. flavescens IFO 3058, Lactobacillus, e.g., L. brevis IFO 3345 and Nocardia, e.g., N. opaca ATCC 4276.

The introduction of the $\Delta^6$-double bond can be performed, e.g., by using a substituted benzoquinone such as chloranil or 2,3-dichloro-5,6-dicyanobenzoquinone (see J. Am. Chem. Soc., 82, 4293 (1960); 81, 5951 (1959)) or by using manganese dioxide (see J. Am. Chem. Soc., 75, 5932 (1953)).

The 1,4,6-trisdehydro-D-homopregnanes of formula I can also be obtained directly by using 2,3-dichloro-5,6-dicyanobenzoquinone or chloranil.

Embodiment (c) of the present process yields 4,6-dienes, 1,4-dienes and 1,4,6-trienes of formula I.

The cleavage of the lactone ring present in the D-homopregnanes of formula V according to embodiment (d) of the present process can be carried out by known methods. For example, by using a base such as potassium hydroxide or sodium hydroxide in a solvent, e.g., an alcohol, such as methanol, ethanol or isopropanol, at a temperature between about 0° C. and the reflux temperature of the mixture, preferably at about 50° C. The salts so obtained, which correspond to the employed base, can be converted into the free acids of formula I by acidification, e.g., by using hydrochloric acid. The latter can be converted into salts by treatment with suitable bases.

Embodiment (d) of the present process yields D-homopregnanes of formula I in which X is hydrogen and Y is hydroxy and salts thereof.

The lactonization of the D-homopregnanes of formula VI or a salt thereof according to embodiment (e) of the present process can be carried out by known methods. For example, by using a strong acid, such as hydrochloric acid, sulfuric acid or p-toluenesulfonic acid in a solvent, e.g., water, an alcohol, such as methanol, or mixtures thereof at a temperature between about −50° C. and 100° C., preferably at room temperature.

The oxidation of the D-homopregnanes of formula VII according to embodiment (f) of the present process can be carried out according to the Oppenauer procedure, e.g., with aluminum isopropylate, with oxidizing agents, such as chromium trioxide, e.g., Jones' reagent, according to the Pfitzner-Moffatt procedure with dimethyl sulfoxide/dicyclohexylcarbodiimide (the initially obtained $\Delta^5$-3-ketone requiring subsequent isomerization to the $\Delta^4$-3-ketone) or with pyridine/sulfur trioxide. When oxidizing agents such as bromine/lithium bromide/lithium carbonate in dimethylformamide are used or when the oxidation is performed according to the Oppenauer procedure in the presence of benzoquinone, the product obtained contains a 3-keto-$\Delta^{4,6}$-function. In order to obtain a 3-keto-$\Delta^{1,4,6}$-compound of formula I, the oxidation is suitably carried out using, e.g., 2,3-dichloro-5,6-dicyanobenzoquinone.

The starting materials of formulas II–VII hereinbefore, insofar as their preparation is not already known or described hereinafter, can be prepared by analogy to known methods or to methods described hereinafter.

The D-homopregnanes provided by the present invention exhibit pharmacological activity. The D-homopregnanes show, among other activities, diuretic activity and are suitable for blocking the action of aldosterone or desoxycorticosterone acetate. Accordingly, they can be used, for example, as potassium-sparing diuretics or for the flushing of edemas. The D-homopregnanes may be administered, for example, in a dosage of from about 0.1 mg/kg to 10 mg/kg per day.

The activity of the D-homopregnanes provided by the present invention can be determined as follows:

The compound to be tested is administered perorally in a gelatin capsule to episiotamized and catheterized dogs. Immediately thereafter the dogs are injected subcutaneously with 0.5 μg/kg of aldosterone. The urine of the dogs is collected over a period of 6 hours. The sodium(Na+)/potassium(K+) ratio calculated from the total excretion is taken as the measure of aldosterone antagonism. When the foregoing experiment was carried out using 7α-acetylthio-6α-methyl-3-oxo-D-homo-17aα-pregna-4,16-diene-21,17a-carbolactone (compound A) and 7α-acetylthio-6α-methyl-3-oxo-D-homo-17aα-pregna-1,4,16-triene-21,17a-carbolactone (compound B) the results given in the following Table were obtained:

TABLE

| Compound | Dosage mg/kg | Na+/K+ in % of the control |
|---|---|---|
| Control | 0 | 100 |
| A | 4 | 210 |
| B | 1 | 244 |
| B | 3 | 510 |
| B | 10 | 652 |

The D-homopregnanes provided by the present invention can be used as medicaments: For example, in the form of pharmaceutical preparations which contain them in association with a compatible pharmaceutical carrier material. The carrier material can be an organic or inorganic inert carrier material suitable for enteral or parenteral administration, such as, for example, water, gelatin, gum arabic, lactose, starch, magnesium stearate, talc, vegetable oils, polyalkyleneglycols, petroleum jelly, etc. The pharmaceutical preparations can be made up in a solid form, e.g., as tablets, dragees, suppositories or capsules, or in a liquid form, e.g., as solutions, suspensions or emulsions. The pharmaceutical preparations may be sterilized and/or may contain adjuvants such as preserving, stabilizing, wetting or emulsifying agents, salts for varying the osmotic pressure or buffers. They can also contain other therapeutically valuable substances.

The pharmaceutical preparations can be prepared by known methods by mixing a D-homopregnane of the present invention with conventional non-toxic, inert, solid and/or liquid carrier materials suitable for therapeutic administration, e.g., the carrier materials previously named, and, if desired, bringing the mixture into the desired dosage form.

The following Examples illustrate the present invention.

EXAMPLE 1

A mixture of 1.0 g of 6-methylene-3-oxo-D-homo-17aα-pregna-4,16-diene-21,17a-carbolactone, 0.5 g of sodium acetate, 50 mg of 5% palladium/carbon and 35 ml of ethanol was heated under reflux for 15 hours. Simultaneously, 2 ml of 0.5% solution of cyclohexene in ethanol were added dropwise per hour. The catalyst was filtered and the filtrate was evaporated in vacuo. The residue was chromatographed on 55 g of silica gel. Elution with methylene chloride/acetone (98:2) yielded 820 mg of pure 6-methyl-3-oxo-D-homo-17aα-pregna-4,6,16-triene-21,17a-carbolactone, melting point 197°–198° C. (from acetone/hexane); $[\alpha]_D^{25} = +41°$ (c=0.1 in dioxan); $\epsilon_{287}=22100$.

The above lactone can also be obtained by acidifying a solution of potassium 17a-hydroxy-6-methyl-3-oxo-D-homo-17aα-pregna-4,6,16-triene-21-carboxylate with dilute hydrochloric acid.

6-Methylene-3-oxo-D-homo-17aα-pregna-4,16-diene-21,17a-carbolactone, used in this Example was prepared as follows:

3-oxo-D-homo-17aα-pregna-4,16-diene-21,17a-carbolactone was converted using pyrrolidine in methanol into the enamine, 3-(1-pyrrolidinyl)-D-homo-17aα-pregna-3,5,16-triene-21,17a-carbolactone. The enamine was treated with formaldehyde in benzene/methanol/water to give 6β-hydroxymethyl-3-oxo-D-homo-17aα-pregna-4,16-diene-21,17a-carbolactone, melting point 246°–249° C.; $[\alpha]_D^{25}=+6°$ (c=0.1 in dioxan). Treatment of the lactone with aqueous hydrochloric acid in dioxan yielded 6-methylene-3-oxo-D-homo-17aα-pregna-4,16-diene-21,17a-carbolactone, melting point 216°–220° C.; $[\alpha]_D^{25}=+175°$ (c=0.1 in dioxan).

EXAMPLE 2

A solution of 1.0 g of 6-methyl-3-oxo-D-homo-17aα-pregna-4,6,16-triene-21,17a-carbolactone in 10 ml of thioacetic acid was heated at reflux for 6 hours. The excess thioacetic acid was evaporated in vacuo and the residue was chromatographed on 100 g of silica gel. Elution with hexane/acetone yielded 0.9 g of pure 7α-acetylthio-6α-methyl-3-oxo-D-homo-17aα-pregna-4,16-diene-21,17a-carbolactone, melting point 215°–217° C. (from acetone/hexane); $[\alpha]_D^{25}=-16°$ (c=0.1 in dioxan); $\epsilon_{237}=19900$.

EXAMPLE 3

A solution of 1.0 g of 7α-acetylthio-6α-methyl-3-oxo-D-homo-17aα-pregna-4,16-diene-21,17a-carbolactone and 0.9 g of 2,3-dichloro-5,6-dicyanobenzoquinone in 50 ml of dioxan was boiled under reflux for 48 hours. The cooled solution was filtered through 20 g of Alox (activity II) and the product was eluted completely with 300 ml of ethyl acetate. The eluate yielded, after evaporation of the solvent, 1.0 g of crude product which was chromatographed on 50 g of silica gel. Elution with hexane/acetone (6:1) yielded 730 mg of pure 7α-acetylthio-6α-methyl-3-oxo-D-homo-17aα-pregna-1,4,16-triene-21,17a-carbolactone, melting point 160°-162° C.; $[\alpha]_D^{25} = -29°$ (c=1.0 in dioxan); $\epsilon_{240} = 17400$.

EXAMPLE 4

A solution of 126 mg of potassium hydroxide (85%) in 0.68 ml of water was added to a solution of 700 mg of 6-methyl-3-oxo-D-homo-17aα-pregna-4,6,16-triene-21,17a-carbolactone in 7 ml of 2-propanol and the mixture was heated to reflux for 30 minutes. The solution was evaporated to dryness in vacuo and the residue was freed from water by addition and evaporation of absolute ethanol. The residue was suspended in 30 ml of ethyl acetate and the product was filtered off under suction. After drying overnight in vacuo at 60° C., there was obtained 800 mg of pure potassium 17a-hydroxy-6-methyl-3-oxo-D-homo-17aα-pregna-4,6,16-triene-21-carboxylate; $[\alpha]_D^{25} = -120°$ (c=0.1 in methanol); $\epsilon_{290} = 22800$.

EXAMPLE 5

A mixture of 1.0 g of 6-methylene-3-oxo-D-homo-17aα-pregna-4,16-diene-21,17a-carbolactone, 200 mg of 5% palladium-on-carbon, 5 ml of benzene and 5 ml of cyclohexene was heated at reflux under argon for 12 hours. The cooled mixture was filtered and the filtrate was evaporated in vacuo. Recrystallization of the crude product from ethanol and acetone gave pure 6β-methyl-3-oxo-D-homo-17aα-pregna-4,16-diene-21,17a-carbolactone, melting point 238°-240° C.; $[\alpha]_D^{25} = +2°$ (c=0.1 in dioxan); $\epsilon_{241} = 15700$.

EXAMPLE 6

2.5 g of 3β-hydroxy-6-methyl-D-homo-17aα-pregna-5,16-diene-21,17a-carbolactone was dissolved in 67 ml of dimethylformamide. Lithium bromide (3.1 g) and lithium carbonate (3.1 g) were added to the mixture. With stirring and gassing with argon the white suspension was warmed to 80° C. At this temperature, was added dropwise within 80 minutes a solution of 2.62 g of bromine in 21 ml of dioxan. After completion of the addition, the yellow-orange suspension was stirred at 80° C. for an additional 30 minutes. The solution obtained was treated with 6 ml of glacial acetic acid, poured into 1000 ml of water and extracted with three 400 ml-portions of ether/methylene chloride (4:1). The organic phases are washed to neutrality with saturated sodium chloride solution, dried over magnesium sulphate and evaporated to dryness. The crude product was purified by chromatography on a 100-fold amount of silica gel with methylene chloride/acetone (98:2). The fractions containing the produce were pooled and recrystallized from acetone/hexane to give 3-oxo-6-methyl-D-homo-1;7aαpregna-4,6,16-triene-21,17a-carbolactone as colorless crystals, melting point 197°-198° C.; $[\alpha]_D^{25} = +41°$ (c=0.1 in dioxan).

The starting material can be prepared as follows:

Dimethylsulphoxonium methylide was treated with 3β-hydroxy-6-methylandrost-5-en-17-one in dimethyl sulphoxide to give 17,20-epoxy-3β-hydroxy-6-methyl-21-norpregn-5-ene. The epoxide was cleaved with ammonia under pressure to give 20-amino-3β,17-dihydroxy-6-methyl-21-norpregn-5-ene. The latter was subjected to Demjanov ring-expansion to give 3β-hydroxy-6-methyl-D-homoandrost-5-en-17a-one which, by bromination with cupric bromide in boiling methanol and susequent cleavage of hydrogen bromide using calcium carbonate in boiling dimethylacetamide, was converted via 17a-bromo-3β-hydroxy-6-methyl-D-homoandrost-5-en-17a-one into 3β-hydroxy-6-methyl-D-homoandrosta-5,16-dien-17a-one. Reaction with the lithium Grignard 3-bromo-propionaldehyde dimethylacetal and subsequent acetylation with acetic anhydride/pyridine yields 3β-acetoxy-21-dimethylacetal-17a-hydroxy-6-methyl-D-homo-17aα-pregna-5,16-diene. The acetal was cleaved with an aqueous 70% acetic acid solution to give the corresponding aldehyde. The aldehyde cyclized spontaneously to give 3β-acetoxy-6-methyl-D-homo-17aα-pregna-5,16-diene-21,17a-carbolactol. Jones oxidation yields the corresponding 21,17a-carbolactone which is saponified with potassium carbonate in methanol to give 3β-hydroxy-6-methyl-D-homo-17aα-pregna-5,16-diene-21,17a-carbolactone.

The following Examples illustrate typical pharmaceutical preparations containing the D-homopregnanes provided by the present invention:

EXAMPLE A

A tablet for oral administration contains the following ingredients:

D-Homopregnane of formula I or salt thereof: 25 mg
Maize starch: 100 mg
Lactose: 50 mg
Polyvinylpyrrolidone: 15 mg
Magnesium stearate: 2 mg

EXAMPLE B

A capsule for oral administration contains the following ingredients:

D-Homopregnane of formula I or salt thereof: 25 mg
Maize starch: 125 mg
Lactose: 125 mg

We claim:

1. A D-homopregnane of the formula

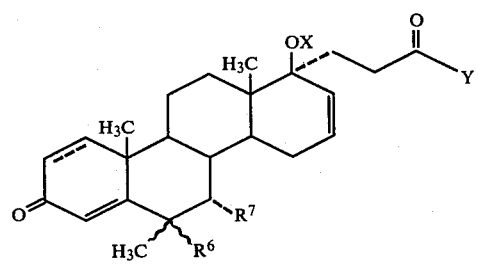

wherein X is hydrogen and Y is hydroxy; $R^6$ is hydrogen; $R^7$ is lower alkanoylthio or aroylthio; and the dotted line in the 1,2-position of the A-ring together with the corresponding solid line denotes a single or double carbon to carbon bond, or a pharmaceutically-acceptable basic addition salt thereof.

* * * * *